(12) United States Patent
Gil et al.

(10) Patent No.: US 8,557,894 B2
(45) Date of Patent: Oct. 15, 2013

(54) WATER-TRIGGERED COLORING OR COLOR CHANGING INDICATOR

(75) Inventors: JunMo Gil, Deajeon (KR); Xuedong Song, Alpharetta, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 792 days.

(21) Appl. No.: 12/640,604

(22) Filed: Dec. 17, 2009

(65) Prior Publication Data
US 2011/0152805 A1 Jun. 23, 2011

(51) Int. Cl.
*C09D 11/00* (2006.01)

(52) U.S. Cl.
USPC ..... 523/160; 604/361; 428/304.4; 428/411.1; 428/523; 428/532; 427/8; 524/378; 524/384; 524/186; 523/161

(58) Field of Classification Search
USPC ........................................... 523/160
See application file for complete search history.

(56) References Cited

U.S. PATENT DOCUMENTS

| | | | |
|---|---|---|---|
| 4,252,845 A * | 2/1981 | Griffiths et al. | 427/273 |
| 5,478,382 A | 12/1995 | Miller et al. | |
| 2005/0120919 A1 | 6/2005 | Davies-Smith et al. | |
| 2005/0287356 A1 | 12/2005 | Li et al. | |
| 2007/0017413 A1 | 1/2007 | Kwan et al. | |
| 2009/0275908 A1 * | 11/2009 | Song | 604/361 |

* cited by examiner

*Primary Examiner* — Doris Lee
(74) *Attorney, Agent, or Firm* — Denise L. Stoker; Vincent T. Kung

(57) ABSTRACT

An ink formulation that includes a reversible color-developing complex formed from a dye precursor molecule having a triarylmethane derivative structure modified with a leaving-group (L) that disassociates from said dye precursor when subjected to environmental conditions of either a neutral or acidic pH value is described. Also the invention pertains to diagnostic indicators or absorbent personal care products that have the ink formulation applied to at least a part of the product.

25 Claims, 2 Drawing Sheets

R = H, alkyl, halogen, alkoxy, amino, alkylamino group substitutes
L = leaving group such as OH, OR, $NR_2$

US 8,557,894 B2

WATER-TRIGGERED COLORING OR COLOR CHANGING INDICATOR

FIELD OF INVENTION

The present invention relates to certain colorant systems that can be triggered by the presence of an aqueous substance. In particular, the invention pertains to a colorant or dye complex that can be activated or deactivated by pH conditions so as to provide a durable, visually observable signal.

BACKGROUND

Many products, including consumer and professional products, can be used more effectively by an end user if they include a feature that informs a particular condition or state of use for the products. For instance, in the area of consumer absorbent products, especially in the diaper, feminine hygiene, or paper tissue markets, manufacturers have recently investigated various ways of providing a wetness sensitive indicator that can give a signal to the consumers or end-users and allows them to change or replace the absorbent products in a timely manner. These color based indicators can provide more satisfaction and enhance the consumer's experience of the products by relaying real time informing about wetness conditions without any additional equipments, such as electronic devices. Such wetness sensing technology can improve levels of hygiene and care, especially for persons who cannot easily communicate to caregivers such as newborn babies or incapacitated patients. For instance, the signal can prevent a baby's or patient's skin from over exposure to moisture which may cause a number of problems such as rashes.

Many kinds of wetness indicating technologies have been described in the literature for consumer products, but none of the currently existing approaches is ideal. An example of a visual wetness indicator is a color indicator. Color indicators can either indicate a change in condition or a degree of use through a change from "no color" to "color" (or vice versa) or through a change from one color to a different color.

Exemplary conditions that could be monitored using a color indicator include physical conditions such as the presence of moisture and chemical conditions such as a change in pH. Exemplary consumer products that could be more effective and deliver more benefits to end users by incorporating a suitable color indicator include absorbent articles, facial tissues, bath tissue, paper towels, household cleaning items and personal cleaning wipes. Exemplary professional products that could be more effective and deliver more benefits to end users by incorporating a suitable color indicator include products for medical use, safety garments, industrial cleaning products and nonwoven materials.

For instance, certain adhesive-based wetness indicators give very poor color contrast, and the indicator colors also can suffer from dye leaching off of its substrate. Other water-dissolved-dye-based wetness indicators suffer from low sensitivity and again low color contrast. Given these shortcomings, workers in the colorant indicator area would welcome a new technical approach to generate durable and highly visually-contrasting colorants. Color indicators are well known and are available in various forms. Desirable performance attributes include durability and good retention (i.e. the color indicator remains where intended and does not bleed or leach out into other components of the product within which it is being used). Depending on the product application, it may also be desirable to have the structure in which the color indicator is used be wettable, but water insoluble. For purposes of applying the color indicator to a component of a product, it may also be desirable to have a color indicator that can be applied in liquid form at room temperature. When the color indicator is in a liquid form at room temperature, the color indicator can be printed (just like an ink composition) onto the desired component of a product. The ink form can make easier demonstration to provide more attractive graphic by being adjusted into current printing methods, such as ink jet, flexographic or gravure methods.

Examples of how color indicators are already incorporated into consumer products include diapers that have wetness sensors. Some of the wetness sensors used in diapers change color to indicate wetness while others lose color in response to wetness (i.e. the color fades or disappears when it is dissolved by water). The concept of incorporating a color-changing composition into a wearable article (such as a disposable diaper) is known in the art. For example, U.S. Pat. No. 7,159,532 issued to Klofta et al. (hereinafter "the '532 patent") is directed to wetness indicating compositions having improved colorant retention and durability for use with wearable articles. The wetness indicating compositions of the '532 patent have a first binding agent and a second binding agent. The first binding agent immobilizes a colorant when the colorant is in its initial color state and the second binding agent immobilizes the colorant when the colorant is in its final color state. The component materials used in the examples provided in the '532 patent are solid at room temperature as indicated by the description that they need to be melted in order to combine them. While the wetness indicating compositions of the '532 patent are capable of changing color in response to a stimulus, they are not capable of being applied to an article in liquid form at room temperature.

While the color-changing compositions known in the art provide certain benefits, there remains a need for a film-forming composition that can be applied to a substrate. There also remains a need for a composition that is durable, has good retention and that shows rapid and dramatic color change when the composition is used in a product. When the purpose of the composition is to detect the presence of wetness, there remains a need for a composition that is water-resistant and water-insoluble. Further, there remains a need for a composition that can be applied, such as by printing, at room temperature so that the composition can be applied to a substrate without heating.

SUMMARY OF THE INVENTION

The present invention relates to color-developing complex that involves a triaryl-methane-based dye precursor derivative in a reaction system that can be adapted for and incorporated into various absorbent products. When formulated into a wetness-indicating ink, the color-developing system is not only printable on various substrates to provide different types of graphic patterns using pH-changing mechanism, but also can provide rapid and dramatic color change upon wetting without dye leaching. In contrast to previous wetness-indicating materials that are limited to changing from colored to colorless or from one color to another, the present colorant system are colorless or near colorless when first applied to a film substrate of an absorbent article. Under predetermined pH conditions, the indicator colorant system can be triggered from the colorless undeveloped or un-reacted state to appear vividly. Although development of a colorless-to-color-appearing wetness indicator has been a great technical challenge, the present invention can offer the consumer a more powerful visual impact with a broadened arrange of potential dramatic signals and patterns which can change from a colorless appearance to bright colored appearance. Moreover, this technology enables manufacturers to offer or use a more varied and wider pallet of novel colors than those appearing or applied before in the wetness indicator technology area, especially in personal care products.

In particular, according to the invention, the ink or colorant composition comprises: about 0.1 to about 12% wt./wt. of a reversible color-developing complex formed from a dye precursor molecule having a triarylmethane derivative structure (1),

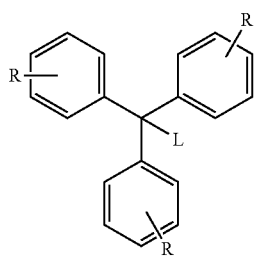

(1)

modified with a leaving-group (L) that disassociates from said dye precursor when subjected to environmental conditions of either a neutral or acidic pH value; b) about 3% to about 50% wt./wt. polymeric binder; c) and about 1% to about 21% wt./wt. of a alkaline pH regulator, all in either a polar or non-polar solvent.

In another aspect, the invention describes to a diagnostic indicator or sensor device that has a substrate with a surface at least partially treated with the ink medium containing the color-developing agent having a triaryl-methane-based dye precursor molecule that is rendered colorless when subjected to alkaline conditions of pH>8, and changes from either being colorless or a pale shade to being colored or a brilliant shade when subject to a fluid sample that has either a neutral or acidic pH value. The indicator or sensor can be integrated or be a part of an absorbent article.

BRIEF DESCRIPTION OF FIGURES

FIG. 2A shows the substrate in its initial state, having the present color-developing ink printed on its surface. FIGS. 2B-2D shows the development of color over time and with increasing amounts of water applied.

DETAILS DESCRIPTION OF THE INVENTION

Section I

Definition

Figure 1:
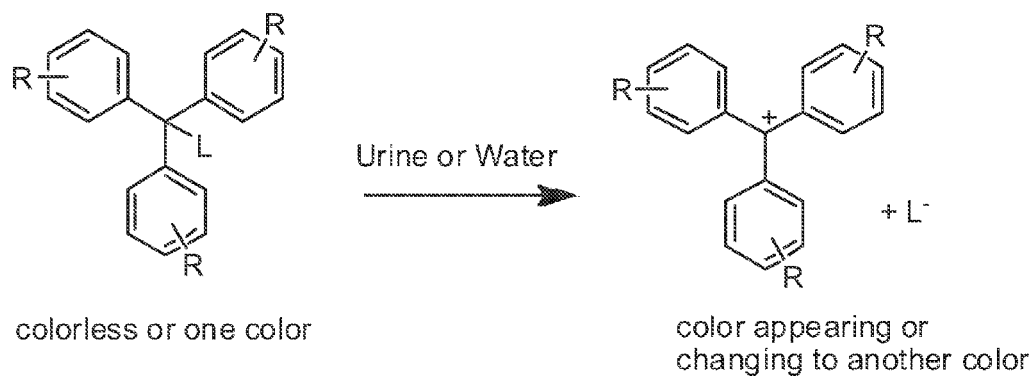
FIG. 1 illustrates a chemical reaction according to the present inventive concept.
Figure 2A:
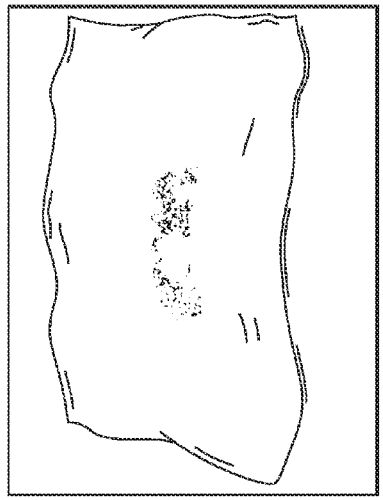
FIGS. 2A-D is a series of schematic representations showing a color-developing indicator material (ink) applied to a substrate surface according to an embodiment of a sensor according to the present invention, and the change in color or pattern from a colorless or nearly colorless state to a state of fully heightened color manifestation when the color-developing ink contacts an aqueous medium.
Figure 2B:
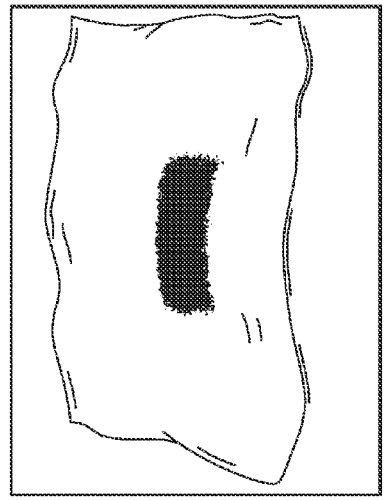
Figure 2C:
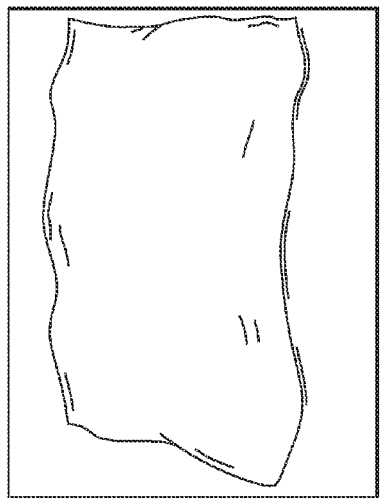
Figure 2D:
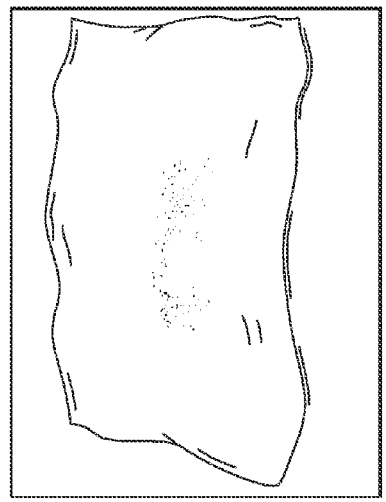

As used herein, the term "colorless-to-colored" refers to a transition state of visual appearance of the present colorant complex or ink medium from a colorless state to a colored state. "Colorless" refers to a visual manifestation that range from an inconspicuous, light, faintly perceivable shade or shadow (in contrast to a background color or pattern) to being nearly invisible to the human naked eye. "Colored" refers to a visual manifestation of a color, hue, shade, or pattern that is generally conspicuous, distinct, and easily perceivable to the human eye.

Section II

Description

In general, the present invention pertains to a color-developing sensor or indicator that can show either the presence or absence of an aqueous-based fluid or water-containing medium. In another aspect, the present invention also pertains to an absorbent article with such a wetness sensor for determining the presence or absence of water in a water-containing media (e.g., blood, menstrual or vaginal fluid, or liquid and solid waste). The sensor is made of at least a substrate and a wetness indicating material which is printed or immobilized on the substrate.

The present invention addresses some of the problematic issues with current wetness indicators. In contrast to many existing wetness indication solutions that transform from colored to colorless when insulted with a liquid, the indicating materials in the present invention turn from colorless to colored and can be more sensitive. This signal in the indicator needs only a relatively small volume of liquid to manifest and is stable without leaching or diffusing in the presence of the liquid.

The present disclosure provides a relatively simple, compact and cost-efficient sensor for accurately detecting the presence or absence of urine. The test result can be visible so that it is readily observed by the person performing the test in a prompt manner and under test conditions conducive to highly reliable and consistent test results.

A

According to this invention, one can employ in an ink formulation a chemical mechanism to create a class of colorless-to-color-appearing wetness indicators. Colorants such as triaryl-methane-based dyes typically have a multi-conjugated cationic molecular structure, which can absorb specific wavelengths of light by the delocalization of cationic or anionic charge through the whole system of conjugated functional groups. The ink can be applied to or printed on a variety of substrates such as in a diagnostic device or absorbent article.

The ink formulation includes: a) a reversible color-developing complex formed from a dye precursor molecule having a triarylmethane derivative structure modified with a leaving-group (L) that disassociates from said dye precursor when subjected to environmental conditions of either a neutral or acidic pH value; b) a polymeric binder; c) and a alkaline pH regulator, all in either a polar or non-polar solvent. The ink formulation may also further include surfactants, wettability adjustor agents, or viscosity adjusters, or resins in the balance or remaining percentage amounts of the formulation. The leaving-group includes: OH, OR, $NR_2$, and wherein R is H, alkyl, halogen, alkoxy, amino, or alkyl-amino group substitutes. The polar solvent can be either an aqueous or organic alcoholic medium. The ink formulation can be a homogenous solution or a mixture.

According to the invention, in the ink formulation, the color-developing complex or dye precursor is present in an amount of about 0.1 to about 12% wt./wt. More typically, the colorant can be present in an amount from about 0.1% or 0.5% wt./wt. to about 8% or 10% wt./wt., in other embodiments between about 1% or 1.3% to about 5% or 6% wt./wt. Also in the formulation, the polymeric binder can be present in a range from about 3% or 5% wt./wt. to about 45% or 50% wt./wt., more typically in an amount from about 4%, 6%, or 10% wt./wt. to about 25%, 30%, 35%, or 40% wt./wt. The pH regulator can be either an organic or inorganic base, and the amount of alkaline pH regulator in the formulation can be from about 1% or 3% wt./wt. to about 18%, or 21% wt./wt. Typically, the amount of base regulator is between about 2 5% or 7% wt./wt. to about 12%, 15%, 17% or 20% wt./wt.

The dye precursor molecule is colorless and stable under alkaline conditions of pH>8; hence, the ink formulation has a pH value greater than 8. The color-development complex is very reactive and manifests color from a neutral or acidic pH value of about 1 or 2 to about 7.0 or 7.8. In an acidic pH value of between about 3 or 4 to about 6.0 or 6.5, desirably about 4-5-6, the color-development complex exhibits good sensitivity and generates vividly or intensifies a color.

When the conjugated structure of the dye molecule is changed by an addition reaction with another molecule, the dye becomes either a colorless or differently colored molecule as a result of the change in the relative degree of bond conjugation and its associated change in the range of visual light absorption. The addition reaction is reversible. The colorless or color-changed molecule can be converted back to the original colored dye molecule by dissociation or regeneration of the molecular conjugated system in the presence of an aqueous substance, according to the chemical reaction illustrated in FIG. 1. The group that was added to render the original colorant molecule colorless is turned into a leaving group (L). Hence, the modified molecular conjugation structure releases the leaving group and reverts to a more thermodynamically stable structure in the presence of water or urine. These kinds of reactions allow one to easily form the colorless carbinol in alkaline media (i.e., pH>8, ≥9 or 10) by an addition reaction on the central methyl cation and reverse it. Furthermore, since many dye molecules in the chemical or food dye formulary that contain a triarylmethane cation structure, the reactions permits manufacturers to take advantage of a wide variety of different dyes that heretofore have either not been or not been successfully incorporated into absorbent products.

Generally, the concept of incorporating color-appearing compositions into an absorbent personal care article (such as a disposable diaper) has not been fully explored. Although some have described technologies that use a color appearing composition of leuco dyes in the presence of water, such as in U.S. Pat. No. 5,130,290, which requires certain essential color developing materials, dye sensitizer and binder, the present invention is different. In contrast, the present system does not require color developers to assist the leuco dye coloring system.

The present inventive concept of a color appearing wetness sensor that functions from a change in the state of the indicator from dryness to wetness, we believe has not been described before. The present invention from a technical aspect uses triarylmethane dye precursors or cation derivatives that are pretreated with base materials and do not require additional color developing materials to generate a change in or manifestation of color. The present invention does not need to release a pre-applied molecule nor reform an original dye molecular structure. This mechanism is based on thermodynamical molecular stability in urine or water presence and pH change of media. The novel classified concept of dye is significantly different because triarylmethane dyes can be regenerates from the precursor cation dye derivatives to provide original color. Many of the dyes according to the invention can be selected from safe food coloring dyes, basic and acid dyes which can be modified to form the triarylmethane-based precursor dye derivatives which are not used as general pH-indicators.

The color-developing complex involves triaryl-methane dye precursor derivatives that include several basic dyes, acid dyes, pH indicator and food coloring dyes which are selected as crystal violet, basic blue 7, basic blue 26, Erio green B, methyl green, N-Naphtholbenzein, light green SF Yellowish (Food green No2), Acid Violet 6B (Food violet No1), BRILLIANT BLUE G, BRILLIANT BLUE R, GUINEA GREEN B, Brilliant Green etc. however the substituted dyes with carboxylate or sulfonate on 2-position of phenyl are excluded from dyes because those dye could not formed colorless or faded color status in this system. Some selected dye molecules are food coloring dyes, which are safe chemically.

Inorganic or organic base may include tetralbutylammonium hydroxide, benzyltrimethylammonium hydroxide, sodium hydroxide, potassium hydroxide, Choline base, Diethyldimethylammonium hydroxide, Dimethyldodecylethylammonium hydroxide, N,N,N,N',N',N'-Hexabutylhexamethylenediammonium dihydroxide, Hexadecyltrimethylammonium hydroxide, Hexamethonium hydroxide, Tetrabutylammonium ethoxide, Tetrabutylphosphonium hydroxide, Tetrahexylammonium hydroxide, Tetramethylammonium hydroxide, Tetraoctylammonium hydroxide, Tetrapropylammonium hydroxide, Tributylmethylammonium hydroxide, Trihexyltetradecylammonium hydroxide, Tetrabutylammonium methoxide and alkyl amide etc. the base is not limited on mentioned one if same mechanism applied for coloring phenomena. The base in the composition should not be a concern since the coloring film is not directly contact with skin and the slight basic condition can be neutralized in water/urine contact, indicated at the same time as color manifests.

The value of pH is used to classify urine as either a dilute acid or base solution. As everyone understands, seven is the point of neutrality on the pH scale, and the lower the pH, the greater the acidity of a solution; the higher the pH, the greater the alkalinity. The glomerular filtrate of blood is usually acidified by the kidneys from a pH of approximately 7.4 to a pH of about 6 in the urine. Depending on the person's acid-base status, the pH of urine may range from 4.5 to 8. The kidneys maintain normal acid-base balance primarily through the re-absorption of sodium and the tubular secretion of hydrogen and ammonium ions. Urine becomes increasingly acidic as the amount of sodium and excess acid retained by the body increases. Alkaline urine, usually containing bicarbonate-carbonic acid buffer, is normally excreted when there is an excess of base or alkali in the body. Secretion of acidic or alkaline urine by the kidneys is one of the most important mechanisms the body uses to maintain a constant body pH.

A highly acidic urine pH can occur when there is acidosis, uncontrolled diabetes, diarrhea, starvation and dehydration, or respiratory diseases in which carbon dioxide retention occurs and acidosis develops. A highly alkaline urine can occur when there is an urinary tract obstruction, pyloric obstruction, salicylate intoxication, renal tubular acidosis, chronic renal failure, or respiratory diseases that involve hyperventilation (blowing off carbon dioxide and the development of alkalosis).

The present invention can be a good tool to detect such disorders. In some situations, for instance, the color change or appearance vary depending on the pH value of the sample urine A more acidic pH can generate a more intense a color or a different color from a neutral pH. For instance, using a dye precursor for Malachite green (carbinol) in i-propanol with demacryl 79 (binder) as applied to a polypropylene film, one can test the relative pH dependency for color appearance under neutral or acidic condition (pH 4.5~7 or distilled water). The test results seem to indicate that below pH 6 the color development kinetics are faster and brighter for color appearing (colorless to green) than neutral saline (of cause, neutral saline works well either but little slow than acidic saline).

B

The color-developing wetness indicator is printable ink-solution type products, which can be applied into several absorbent articles or nonwoven material for consumer products by direct printing on it. The ink can be applied generally over the entire substrate surface or at discrete localized spots on the substrate. The ink can be applied as a coating either in a monochromic color scheme alone, bi-chromic, or in multiple colors, or printed either in various shapes and sizes, graphics of patterns or alpha numeric symbols and/or words, or combinations thereof.

The useful substrates in the invention can vary. The substrates can be porous and hydrophobic films and sheet materials, or cellulosic-based substrates such as fiber fluff, paper tissues, paper sheets or towels and wipers. The substrates can also be nonporous plastic films and sheets, such as polyolefin films, or nonwoven materials. Examples of polyolefin films include polyethylene and polypropylene films, or modified polyethylene and polypropylene films. The substrates may be a part of an outer cover film of an absorbent article such as a diaper, adult incontinence article, or feminine hygiene pad.

Depending on the particular nature of the substrate, the indicator composition would require addition of other ingredients to immobilize or make the color ink agent adhere to the substrate. In addition to the color-developing complex, the composition also may contain wettability enhancing agents such as surfactants and/or water-miscible or hydrophilic polymers, or water-soluble salts. Furthermore, the composition may also contain other additives to adjust viscosity, surface tension, or other physical and chemical properties. Alternatively, the substrates can be treated with different materials to modify their surface properties before the deposition of the composition to improve the adhesion of the composition. According to certain embodiments, a wettability enhancing agent is also applied in the color ink formulation. The wettability enhancing agent can be a surfactant or a mixture of surfactants. The surfactants can be non-ionic surfactants or ionic surfactants. The ionic surfactants can be either positively charged or negatively charged. The examples of non-ionic surfactants include alkyl poly(ethylene oxide) such as copolymers of poly(ethylene oxide) and poly(propylene oxide) (commercially called Poloxamers or Poloxamines), alkyl polyglucosides such as octyl glucoside and decyl maltoside, fatty alcohols such as cetyl alcohol, oleyl alcohol, cocamide MEA and cocamide DEA. The examples of ionic surfactants include anionic (e.g., based on sulfate, sulfonate or carboxylate anions) surfactants such as s (SDS), ammonium lauryl sulfate and other alkyl sulfate salts, Sodium laureth sulfate, also known as sodium lauryl ether sulfate (SLES), Alkyl benzene sulfonate, Soaps, or fatty acid salts; and Cationic (e.g., based on quaternary ammonium cations) surfactants such as Cetyl trimethylammonium bromide (CTAB) a.k.a. hexadecyl trimethyl ammonium bromide, and other alkyltrimethylammonium salts, Cetylpyridinium chloride (CPC), Polyethoxylated tallow amine (POEA), Benzalkonium chloride (BAC), Benzethonium chloride (BZT); or Zwitterionic (amphoteric) surfactants such as Dodecyl betaine, Dodecyl dimethylamine oxide, Cocamidopropyl betaine, Coco ampho glycinate. Alternatively, the wettability enhancing agents may also be hydrophilic molecules. The hydrophilic molecules may be small molecules such as sucrose, glucose and glycerol. The hydrophilic molecules may also be polymers such as polyethylene glycol and its copolymers.

The wetness ink is composed with several components as triarylmethane dye precursor derivatives, inorganic or organic base and binder in aqueous media. Binders that may be incorporated in the ink formulation, for example, may include acrylate/acrylamide copolymers and copolymers of vinylpyrrolidone and dimethylaminopropyl methacrylamide etc. Since one of the uses of this invention is for a wetness indicator, hence the binder's properties are preferred to be either insoluble or less reactive in water so as to prevent it dissolving out the indicator when in contact with aqueous-based media. The binder could be modified or incorporated with a commercialized varnish material or other encapsulating materials.

The present invention can be readily applied into manufacturing process because it involves a simple, single phase ink used in production, and can be applied in a single layer forming a film on the substrate directly. Consumer products that can be potentially integrated with a color based direct state indicators can use the present color-developing complex.

C

In accordance with the present disclosure, one or more sensors described herein can also be integrated into an absorbent article. An "absorbent article" generally refers to any article capable of absorbing water or other fluids. Examples of some, absorbent articles include, but are not limited to, personal care absorbent articles, such as diapers, training pants, absorbent underpants, incontinence articles, feminine hygiene products (e.g., sanitary napkins), swim wear, baby wipes, and so forth; medical absorbent articles, such as garments, fenestration materials, under-zones, bed-zones, bandages, absorbent drapes, and medical wipes; food service wipers; clothing articles; and so forth. Materials and processes suitable for forming such absorbent articles are well known to those skilled in the art. Typically, absorbent articles include a substantially liquid-impermeable layer (e.g., outer cover), a liquid-permeable layer (e.g., bodyside liner, surge layer, etc.), and an absorbent core.

A sensor for detecting the presence of an aqueous-based liquid that has a substrate with at least one type of wetness indicating material immobilized or printed on a layer of the substrate. The indicating material contains at color-developing complex according to the present invention. As mentioned, the indicating material on the substrate normally does not show a strong color in its dry state. The colorless or pale appearance of the indicating material turns more apparent or vibrant when in contact with water-containing media. The water-containing liquid can be either bodily fluids or waste, such as mucus, urine or fecal matter (BM).

The indicating material is on a layer of the substrate that is either on a top sheet of the substrate or within an undersheet that is visible to a caregiver. The indicating material further contains a wettability enhancing agent, or a hydrophilic water-soluble agent. The indicating material is applied either at discrete localized spots on the surface of said substrate or generally over the entire substrate surface. Alternatively, the indicating materials are printed in different patterns and shapes on the substrate. The substrate can be printed with multiple indicating materials on different portion of the substrate.

The wetness sensor may be composed of solid substrate on which is deposited with a colored chemical composition. The solid substrate can be any substrate that allows a deposition of the indicator composition to exhibit a color. The solid substrates may be porous or may not be porous. Examples of the solid substrate include, but not limited to, porous tissues, papers, polymeric films, metals, wood, plastics, rubbers, non-woven materials and woven materials.

Section II

Examples

The present disclosure can be better understood with reference to the following empirical examples:

Examples

1) Into about 0.5 ml solution of 10% Dermacryl 79, we added and mixed by vortexing about 0.1 ml benzyltrimethyl ammonium hydroxide 40 wt % in water solution and 0.0037 g crystal violet. A light, faded gray ink solution was formed and was applied as a film layer on a non-porous polypropylene film, such as the outer cover of a HUGGIES® diaper. Once air-dried, the ink turned largely colorless. When contacted with synthetic urine, the film color changed and appeared as a violet color.

2) Into about 0.5 ml solution of 10% Dermacryl 79 and Brilliant Blue R 0.0055 g, we added and mixed by vortexing about 0.1 ml benzyltrimethyl ammonium hydroxide 40 wt % in water solution, which resulted in a reddish brown solution. The color faded to yellow in an ink solution after about three days (~72 hours time to equilibrate). The ink solution was applied onto a translucently white or clear polypropylene film where the ink appeared to be either colorless or had a light, pale shade after drying in ambient, open air conditions. The colorless ink pattern appeared as violet when insulted with a saline solution.

3) Into about 0.5 ml solution of 10% Dermacryl 79 and Guinea Green B 0.0044 g, we added and mixed by vortexing about 0.1 ml benzyltrimethyl ammonium hydroxide 40 wt % in water solution, resulting in a pale yellow solution within about one hour. The resulting solution was applied onto a translucently white or clear polypropylene film and appeared to be either colorless or very faintly colored, after drying under ambient, air open conditions. The color of the applied ink pattern turned to a sky blue color when insulted with a saline solution.

4) Into 0.5 ml solution of 10% Dermacryl 79 and Basic blue 7 0.0045 g, we added and mixed 0.1 ml benzyltrimethyl ammonium hydroxide 40 wt % in water solution. The resulting mixture appeared as a reddish brown solution, the color of which turned to a faded yellow ink solution after about 24 hours. The ink solution was printed as a pattern on a polypropylene film, and appeared colorless after drying in ambient, air open conditions. When insulting with a saline solution, the printed color pattern turned a blue color.

5) Into 0.5 ml solution of 10% Dermacryl 79 and Basic green 1 0.0045 g, we added and mixed 0.1 ml benzyltrimethyl ammonium hydroxide 40 wt % in water solution. The resulting mixture provided a colorless solution after about one hour. The ink solution was printed as a pattern color on a polypropylene film, and appeared colorless after dryness in ambient, air open conditions. The color of the printed pattern turned to green when insulted with a saline solution.

The present invention has been described in general and in detail by means of examples. Persons of skill in the art understand that the invention is not limited necessarily to the embodiments specifically disclosed, but that modifications and variations may be made without departing from the scope of the invention as defined by the following claims or their equivalents, including other equivalent components presently known, or to be developed, which may be used within the scope of the present invention. Therefore, unless changes otherwise depart from the scope of the invention, the changes should be construed as being included herein.

We claim:

1. An ink formulation comprising: a) about 0.1 to about 12% wt./wt. of a reversible color-developing complex formed from a dye precursor molecule having a triarylmethane derivative structure (1),

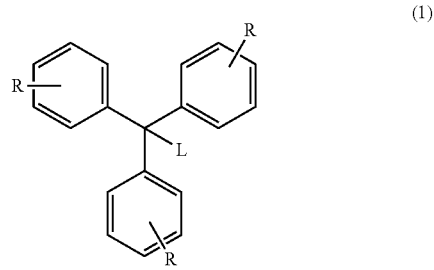

modified with a leaving-group (L) that disassociates from said dye precursor when subjected to environmental conditions of either a neutral or acidic pH value; b) about 3% to about 50% wt./wt. polymeric binder; c) and about 1% to about 21% wt./wt. of a alkaline pH regulator, all in either a polar or non-polar solvent.

2. The ink formulation according to claim 1, wherein said ink formulation may further include surfactants, wettability adjustor agents, or viscosity adjusters, or resins.

3. The ink formulation according to claim 1, wherein said leaving-group includes: OH, OR, $NR_2$, and wherein R is H, alkyl, halogen, alkoxy, amino, or alkyl-amino group substitutes.

4. The ink formulation according to claim 1, wherein said dye precursor molecule is colorless and stable under alkaline conditions of pH>8.

5. The ink formulation according to claim 1, wherein said ink formulation has a pH value greater than 8.

6. The ink formulation according to claim 1, wherein said neutral or acidic pH value ranges from about 2 to about 7.8.

7. The ink formulation according to claim 5, wherein said color-development complex manifests vividly color in an acidic pH value of between about 4 to about 6.5.

8. The colorant complex according to claim 1, wherein said dye precursor is present in an amount from about 0.5% to about 10% wt/wt.

9. The mixed ink formulation according to claim 7, wherein said dye precursor is present between about 1% to about 6% wt./wt.

10. The ink formulation according to claim 1, wherein said polar solvent is either an aqueous or organic alcoholic medium.

11. The ink formulation according to claim 1, wherein said pH regulator is either an organic or inorganic base.

12. The ink formulation according to claim 1, wherein said ink formulation is a homogenous solution.

13. The ink formulation according to claim 1, wherein said polymeric binder is selected from: acrylate/acrylamide copolymers and copolymers of vinylpyrrolidone and dimethylaminopropyl methacrylamide.

14. An absorbent article comprising:
an outer cover layer, a liquid permeable liner layer, and an absorbent body between the outer cover layer and the liner layer;
a substrate having an inner and outer surface forming at least part of said outer cover layer, said substrate situated outward from said absorbent body and is transparent or translucent from said inner surface to said outer surface;
a reversible color-developing complex admixed in the ink formulation of claim 1, said color-developing complex has a dye precursor molecule having a triarylmethane derivative structure (1),

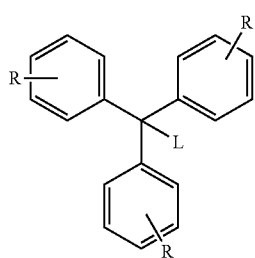

(1)

modified with a leaving-group (L) that disassociates from said dye precursor when subjected to environmental conditions of either a neutral or acidic pH value, wherein the ink is applied to said inner surface of at least part of said substrate, and which manifests a colorless-to-colored visual signal when interacted with a medium having an acidic or neutral pH.

15. The absorbent article according to claim 14, wherein said absorbent article is a diaper, a feminine hygiene article, a paper tissue, such that that is rendered colorless when subjected to alkaline conditions of pH>8, and changes from either being colorless or a pale shade to being colored or a brilliant shade when subject to a fluid with either a neutral or acidic pH value.

16. The absorbent article according to claim 14, wherein said leaving-group (L) includes: OH, OR, $NR_2$, wherein R is H, alkyl, halogen, alkoxy, amino, alkyl-amino group substitutes.

17. The absorbent article according to claim 14, wherein said dye precursor molecule is rendered colorless when subjected to alkaline conditions of pH>8, and changes from either being colorless or a pale shade to being colored or a brilliant shade when subject to a fluid sample that has either a neutral or acidic pH value.

18. The absorbent article according to claim 14, wherein said colorant complex changes from colorless to colored or from a first color to a second color when assaulted with a fluid having either a neutral or acidic pH value.

19. A method of generating a colorless to colored wetness indicator, the method comprising: a) providing the ink formulation of claim 1 a colorant complex having a triaryl-methane-based dye precursor molecule that is rendered colorless when subjected to alkaline conditions of pH>8, said triaryl-methane-based dye precursor molecule has a structure modified with a leaving-group that disassociates from said dye molecule when subjected to environmental conditions of either a neutral or acidic pH value; said leaving-group includes: OH, OR, $NR_2$, wherein R is H, alkyl, halogen, alkoxy, amino, alkyl-amino group substitutes; b) treating at least partially a surface of a film-based substrate with said ink medium; c) subjecting said treated substrate to a fluid with either a neutral or acidic pH value; and d) observing a development of colored signal from said treated substrate.

20. The method according to claim 19, wherein said treating involves either applying or printing said ink medium in a predetermined pattern or design on said substrate surface.

21. The method according to claim 19, wherein said fluid with a neutral or acidic pH value is urine.

22. A diagnostic indicator device comprising: a substrate with a surface at least partially treated with the ink formulation of claim 1 containing color-developing agent having a triaryl-methane-based dye precursor molecule having a structure (1) with a leaving group (L),

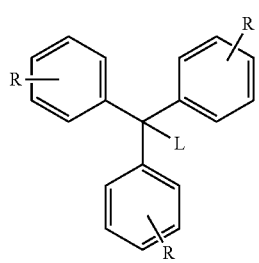

(1)

wherein the triaryl-methane-based dye precursor molecule is rendered colorless when subjected to alkaline conditions of pH>8, and changes from either being colorless or a pale shade to being colored or a brilliant shade when subject to a fluid sample that has either a neutral or acidic pH value.

23. The indicator device according to claim 22, wherein said leaving-group (L) disassociates from said dye molecule when subjected to environmental conditions of either a neutral or acidic pH value; said leaving-group includes: OH, OR, $NR_2$, wherein R is H, alkyl, halogen, alkoxy, amino, alkyl-amino group substitutes.

24. The indicator device according to claim 22, wherein said substrate is polypropylene, polyethylene or cellulose based films or sheets.

25. The indicator device according to claim 22, wherein said fluid sample is urine.

* * * * *